US006482652B2

(12) United States Patent
Furlong et al.

(10) Patent No.: US 6,482,652 B2
(45) Date of Patent: Nov. 19, 2002

(54) BIOLOGICAL PARTICLE SORTER

(75) Inventors: Eileen Furlong, Mountain View, CA (US); David Profitt, Los Altos, CA (US); Matthew Scott, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/814,345

(22) Filed: Mar. 21, 2001

(65) Prior Publication Data

US 2001/0036668 A1 Nov. 1, 2001

Related U.S. Application Data

(60) Provisional application No. 60/191,693, filed on Mar. 23, 2000.

(51) Int. Cl.[7] .......................... G01N 33/48; G01N 21/76
(52) U.S. Cl. .......................... 436/63; 436/164; 436/172; 422/73; 422/82.08; 209/3.1; 209/552; 209/576; 209/577; 209/906; 356/436; 356/441; 356/442
(58) Field of Search .......................... 436/63, 164, 172, 436/72; 422/73; 209/3.1, 552, 576, 577, 579, 587, 588, 906; 356/432, 436, 440, 441, 442

(56) References Cited

U.S. PATENT DOCUMENTS 5,713,473 A   2/1998   Satake et al. ............... 209/580
5,880,474 A   3/1999   Norton et al. ............ 250/458.1
2001/0036668 A1 * 11/2001  Furlong et al. ................ 436/63

FOREIGN PATENT DOCUMENTS

WO   WO 97/49925 A1   12/1997
WO   WO 00/11449      3/2000

OTHER PUBLICATIONS

Furlong et al. (Feb. 2001), "Automated Sorting of Live Transgenic Embryos," *Nature Biotechnology*, vol. 19:153–156.
Krasnow et al. (Jan. 4, 1998), "Whole Animal Cell Sorting of Drosophila Embryos." *Science*, vol. 251:81–85.

* cited by examiner

*Primary Examiner*—Maureen M. Wallenhorst
(74) *Attorney, Agent, or Firm*—Pamela J. Sherwood; James S. Keddie; Bozicevic, Field & Francis LLP

(57) ABSTRACT

An automated particle sorter having a fluid flow path, which places single biological particles in an optical cuvette. An exciting light irradiation system having a light source emits a source of light through the cuvette. The light excites a fluorescent substance present on the particle, and the emitted light is detected by a light detection apparatus containing at least two detection elements for measuring the fluorescence emitted from the fluorescent substance. A light separation element separates the fluorescence from the exciting light. A data processor compares the signal received from the fluorescent light; and from the background autofluorescent signal, and according to pre-set parameters, controls the position of a collection conduit between two set points. The first being a collection set point for the collection of objects having a first phenotype and the second being a set point for the collection of objects having a second phenotype.

15 Claims, 5 Drawing Sheets

BIOLOGICAL PARTICLE SORTER

CROSS-REFERENCE TO RELATED APPLICATIONS

This application claims priority to U.S. Provisional Patent Application No. 60/191,693, filed Mar. 23, 2000.

GOVERNMENT SUPPORT

This invention was made with Government support under contract N00014-98-10689 awarded by the Navy ONR. The Government has certain rights in this invention

INTRODUCTION

In many areas of research, the ability to separate animals or other large biological particles according to their phenotype is desirable. For example, there are now thousands of mutant Drosophila strains available. In fact, a project is underway to isolate a mutation in every Drosophila gene. However, in a breeding population three-quarters of the animals carry at least one normal chromosome and only one-quarter carry two mutant chromosomes. The ability to separate populations of mutant embryos from their normal siblings would greatly enhance the molecular and biochemical studies of these newly identified and uncharacterized genes.

Present technology in cell sorting is limited to the isolation of individual cells. Through the use of a flow cytometer, cells are sorted on the basis of their levels of fluorescence. The cells are placed in a laminar stream of liquid and flowed through a small opening where a jet in air is formed. When this jet is mechanically vibrated, it breaks into regularly spaced drops, such that there is approximately one cell per drop. A cell is then sorted or isolated by putting an electric charge on the droplet of water, which can then be deflected according to the charge. However, large biological particles, such as embryos or small animals, are heavy and difficult to deflect accurately by such a method. The present invention addresses this problem by eliminating the need for deflection.

Relevant Literature and Prior Art

Flow cytometers for use in sorting single cells are described in a number of publications. Exemplary is U.S. Pat. No. 5,880,474, issued Mar. 9, 1999, and the references cited therein. Krasnow et al. (1991) *Science* 251:81–85 describes the use of a conventional cell sorter to analyze the cells of a dissociated Drosophila embryo.

Other particle sorters have been described in the art. For example, Satake et al., U.S. Pat. No. 5,713,473, issued Feb. 3, 1998 describes a conveyer belt type sorter for beans.

Other art in this field is evident in the COPAS™ fluorescence based sorter (manufactured and sold by Union Biometrica, Somerville, Mass.). Unlike the present invention, the COPAS sorter uses a fluid switch to interrupt and redirect particle flow. See International Patent application WO 00/11449.

SUMMARY OF THE INVENTION

An automated particle sorter is provided, which allows the separation of large multicellular biological particles, including embryos, small organisms and the like. The particle sorter provides a means of sorting multicellular aggregates that are too large to be sorted with an electrostatic deflection flow cytometer. The particle sorter comprises a fluid flow path, which places single biological particles in an optical cuvette. An exciting light irradiation system directs a source of light through the cuvette. The light excites a fluorescent substance present on the particle, and the emitted light is detected by a light detection apparatus comprising at least two detection elements for measuring the fluorescence emitted from the fluorescent substance. A light separation element, such as a dichroic mirror, is employed to separate the fluorescent light from the exciting light. A data processor compares the signal received from the fluorescent light; and from the background autofluorescent signal, and according to pre-set parameters, controls a mechanical switch that alters the position of a collection conduit between two set points. The conduit is composed of at least two tubes separated by a very thin central wall, e.g. a membrane. Sorting is achieved by moving the appropriate tube under the fluid stream. The tubes can, in turn lead to other collection vessels.

DETAILED DESCRIPTION OF THE EMBODIMENTS

Figure 1:
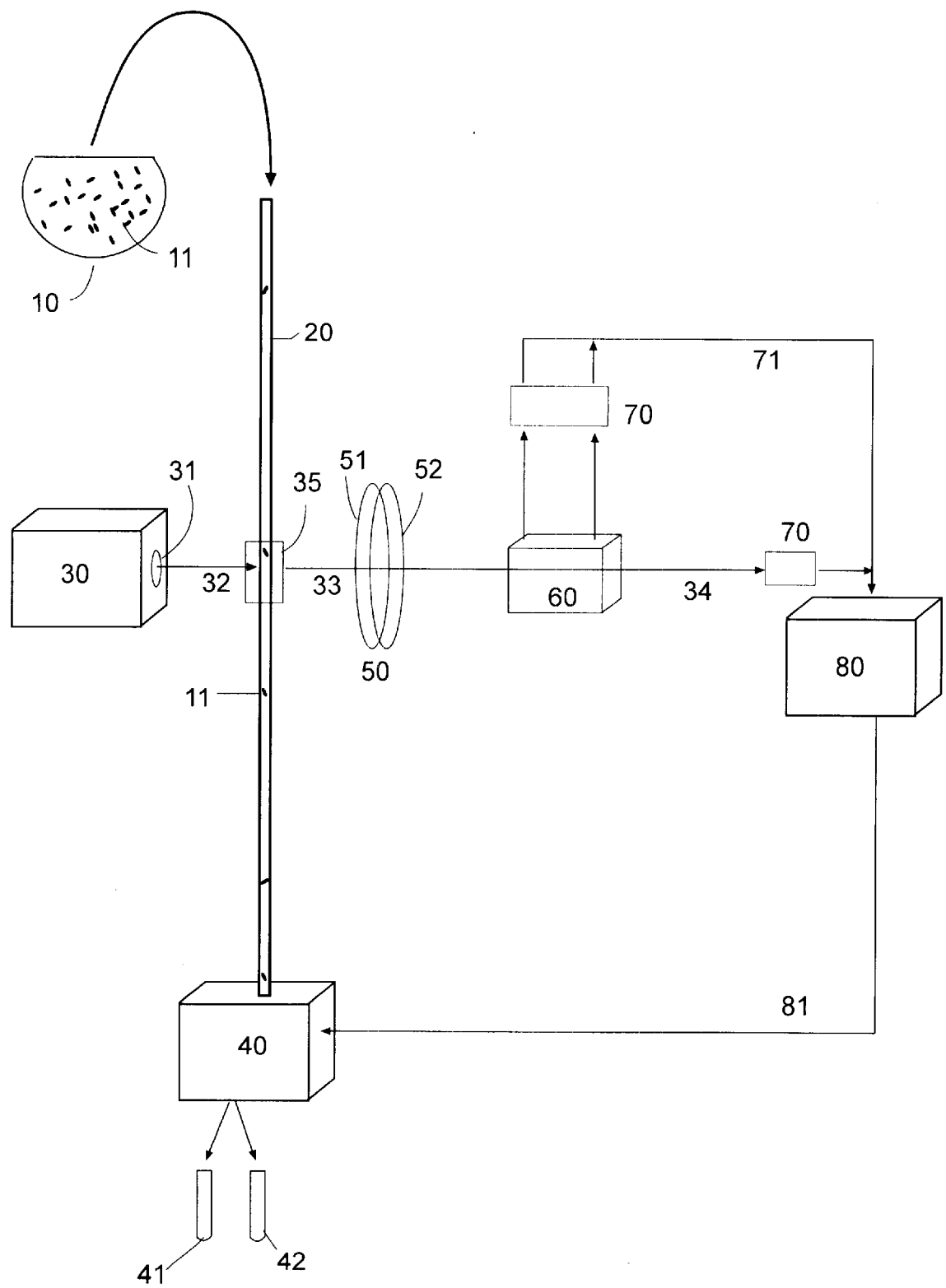
FIG. 1 is a diagram of the particle sorter.

The particle sorter of the invention provides a means of sorting multicellular aggregates, such as small animals and embryos, that are too large to be sorted with a conventional, electrostatic deflection, flow cytometer. The particles are suspended in a solution, which is pumped through a narrow flow path in which the particles are dispersed so as to isolate single particles along the path. The flow path enters an optical cuvette, through which an exciting light is emitted. The light passes through the cuvette, and if a fluorescent substance is present in the cuvette, it will emit fluorescence. One or more partial reflection mirror such as dichroic mirrors are employed to separate the fluorescent light from the exciting light. A light detection system comprising one or more light detecting elements, e.g. photodiodes, photomultiplier tubes, etc., receives the light and transmits the information to a data processor. The data processor controls a switching mechanism that alters the position of a collection conduit between two set points. The first is a collection set point for the collection of desired, or saved, objects and the second is a set point for the collection of waste. The conduit is composed of at least two tubes separated by a very thin central wall, e.g. a membrane separation. Sorting is achieved by moving the appropriate tube under the fluid stream.

An object of the invention is to provide a means of automated separation of a sub-population of embryos of a given phenotype from a larger population of embryos. The sorter can automatically separate whole embryos that express a fluorescent protein from those that do not. The invention allows the isolation of large quantities of genotyped embryos and will facilitate the ability to study genes and their mutations at a whole genome level.

The invention finds particular use in the sorting of biological particles that are too large to be sorted by conventional flow cytometry. Such particles are typically greater than the size of a single cell, and may be as large as an embryo. For example, a Drosophila embryos is about 1 mm in length and about 0.1–0.2 mm in diameter. Such large particles will usually comprise at least about 10 cells, more usually at least about $10^2$ cells, frequently as many as $10^3$ cells, and may comprise greater than $10^4$ cells.

One may use the sorter in drug testing, to determine the reversion of mutant phenotypes, including embryonic phenotypes, using pharmacological agents. The sorted particles can be used for the isolation of genetic material, including mRNA and DNA, particularly for the synthesis of cDNA, which is then utilized in the construction of libraries, as probes, for the synthesis of microarrays, etc. Proteins can be isolated from the sorted populations to determine multiprotein complex stability, protein processing and subcellular localization.

In one embodiment of the invention, the sorter is used in the separation of Drosophila embryos. In order to maintain mutations in Drosophila, the chromosome carrying the mutation is in trans to a special chromosome termed the "balancer chromosome" which ensures that the mutation is inherited in the next generation. As a consequence of this only 25% of the embryos produced from these adults will contain the homozygous mutation. Using current technology, in order to conduct molecular and pharmaceutical experiments, tens of thousand of homozygous mutant embryos would have to be hand sorted in order to separate them from the 75% of the population that contain the balancer chromosome. Due to the time consuming and laborious task of hand sorting embryos, the level of experimentation has been severely restricted.

Balancer fly strains are available that carry a gene encoding a green fluorescent protein (GFP), and therefore it is possible to recognize in living embryos the population of homozygous mutants, as they will not contain GFP.

The animals can also be engineered to contain other detectable markers. For example many fluorescent proteins such a *A. Victoria* green fluorescent protein and derivatives thereof have been described in the art. Epitopes not normally found in the animal can be expressed and stained with a fluorescent marker. Alternatively, enzymes such as -galactosidase can be expressed and detected by substrate modification. Commonly used bioluminescent reporters emit in the blue to yellow-green range (250–560 nm). Currently, luciferase genes from a wide variety of vastly different species, particularly the luciferase genes of *Photinus pyralis* (the common firefly of North America), *Pyrophorus plagiophathalamus* (the Jamaican click beetle), *Renilla reniformis* (the sea pansy), and several bacteria (e.g., *Photorhabdus luminescens* and *Vibrio* spp), are used as luminescence reporter genes. Amino acid substitutions in the active sites of luciferase clones may be exploited to alter wavelength of emission (Kajiyama et al. (1991) *Prot. Eng.* 4:691).

The ability to routinely isolate mutant embryos can also be applied to drug testing. The sorter of the invention is used to dispense a fixed number of embryos into one or more containers, e.g. tubes, plates comprising multiple wells, and the like. For example, the save tube can be exchanged for a narrow tube or funnel to sort the embryos into wells, where a robotic arm may be utilized for manipulation of the plate. Different drugs or different concentrations of the same drug can then be added to each container or well using a robot pipetter. The sorter therefore allows pharmaceutical screens in mutant embryos for potential drugs that can reverse the effects of mutations causing a wide variety of defects, e.g. tumors, neuron path finding, aging and longevity, and sterility defects. Further, the sorted embryos can be used as a source of nucleic acids, e.g. to make probes, cDNA libraries, and the like.

FIG. 1 illustrates the general features of the particle sorter. The biological particles 11 are suspended in solution in a particle chamber 12. The embryos can be kept in suspension using a magnetic stir bar that is placed on a pin in order to prevent crushing the embryos. The suspension is pumped through a narrow flow path 20. The flow path is an elongated member of any suitable cross-sectional geometry, and a diameter that permits even flow of the particles while maintaining a separation of individual particles. Preferred is a square or rectangular cross-section, although circular, oval, etc. geometries may also find use.

In order to achieve the goal of delivering the particles in a single file manner, the inside dimensions of the delivery tube must be such that two particles cannot exist side by side. Tubing with such small dimensions can cause high resistance to fluid flows, necessitating either high pressures or excessively slow flow rates. In one embodiment of the invention, relatively large diameter tubing is used for the collection and transfer of the particles then transitioning gradually to a smaller dimension glass detection tube. This gradual transition allows the particles to accelerate before entering the much faster fluid flow of the small glass tube, thereby reducing the frequency of clogging.

The concentration of particles in the suspension is adjusted to a predetermined level in order to permit passage of a single particles through the flow path leading to the optical cuvette. Particles are initially added to a high-density chamber. A suspension of the high density particles is pumped into a low-density chamber, and then moves through the exit tube to the optical cuvette. If the sorting rate drops below a defined threshold, the computer sends a signal to a fluid valve, which opens and closes. This fluid valve then diverts the fluid flow to the high-density chamber. Fluid will then leave this chamber and enter into the low-density chamber, resulting in the addition of particles to the low-density chamber. When the rate of particle sorting increases to the defined threshold, the computer will send a signal back to the valve and re-direct the fluid flow to the low-density particle chamber. This will stop the addition of more particles.

The particle is pumped through the flow path to an optical cuvette 35. The optical cuvette permits passage of light 32 emitted from a light irradiation system. The light irradiation system comprises a light source 30 and a filter 31. When a particle 11 is present in the cuvette, the light will strike it. If a fluorescent dye or protein is present it will be excited to emit fluorescence with a wavelength longer than that of the excitation light. This fluorescence is collected by the focusing optics 50, shown here as a series of lenses 51 and 52.

After the particles flow through the flow cell they drip from the end of the cuvette. In one embodiment of the invention a fluid ring is placed over the end of the cuvette. For example, a metal ring can be firmly attached onto the end of the cuvette via screws. The ring injects fluid from a peristaltic pump into the particle stream as it exits the glass tube, resulting in a high velocity stream of fluid exiting its orifice. The drop containing the particle enters this high speed stream of solution. The collection conduit moves below this stream to sort the particles, but never touches the end of the cuvette-fluid ring. Increasing the fluid flow after the point of detection has two advantages: it allows the embryos to travel at a much slower rate through the point of detection and it allows the sorting switch to operates at moderate speeds, greatly simplifying its design.

The fluorescence is transmitted through a light separation element 60. The light signal is received by the detection system, and the output signal 71 received by a data processor 80. The data processor analyzes the information and determines according to pre-set parameters which collection device to sort the particle into. The data processor may calculate a plurality of characteristic parameters, indicating characteristics of each particle based on the generated signal; distribution preparation device for preparing a distribution of the characteristic parameters and displaying the distribution on the display; data storage device for storing information; decision device for comparison of signals, etc. Typically the sorter will utilize a microcomputer comprising a signal processing circuit, a CPU, a ROM and a RAM. The data processor then controls a mechanical switch 40, which moves the collection conduit 46 to intercept the flow of particles. The sorted particles may then be further led to collection vessels 41 and 42.

Figure 2:
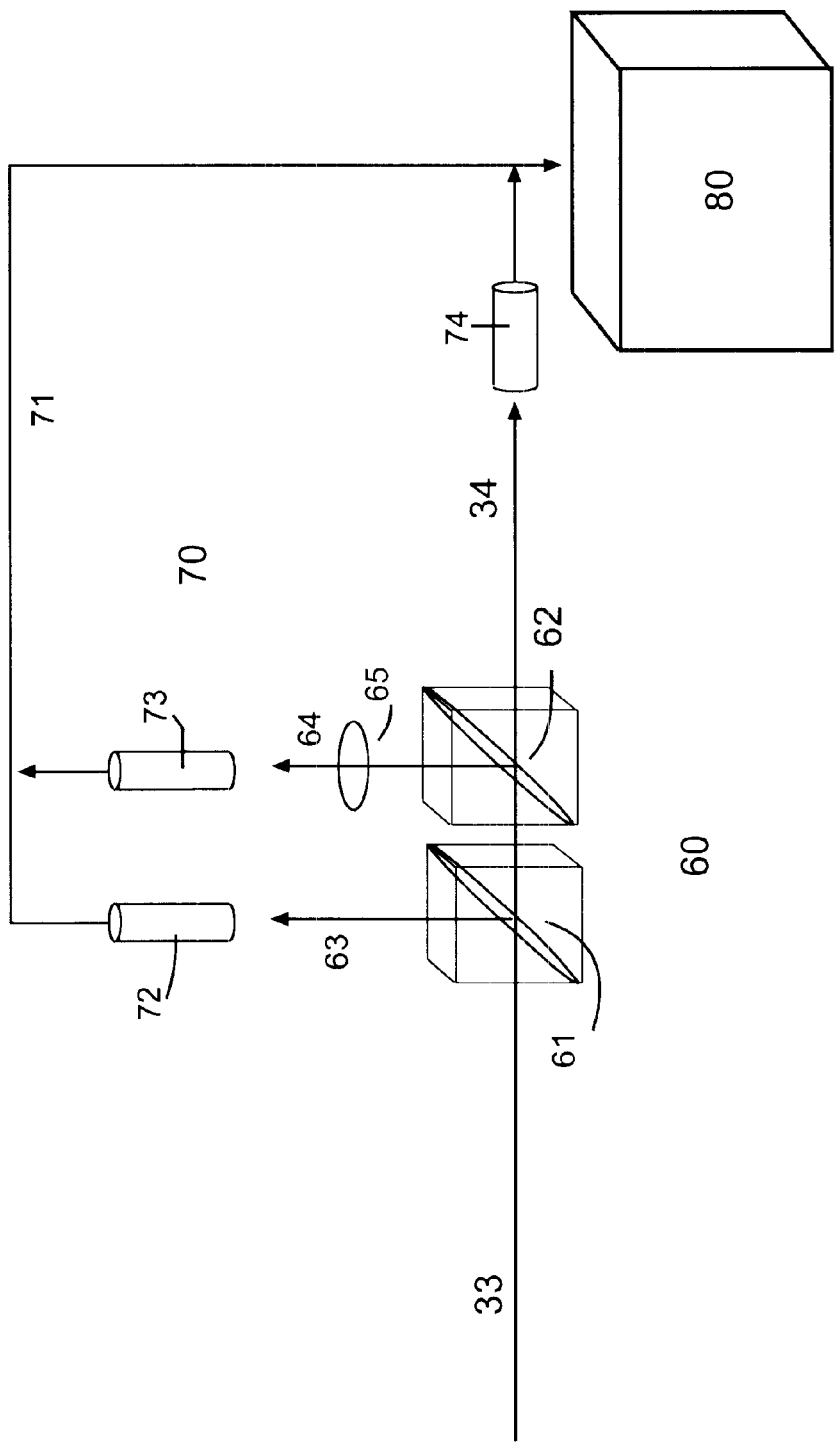
FIG. 2 is an expanded view of the light detection apparatus.

FIG. 2 shows a more detailed view of light detection system. The emitted light 33 is directed to a light separation element 60, which may include one or more partial reflection mirrors such as dichroic mirrors, and combination prisms, and may be any article that transmits a part of fluorescence light and reflects the rest of the fluorescence light. A transparent plate such as an optical glass plate and a quartz glass plate are useful therefore when the intensity of the fluorescence is sufficiently high. Generally, however, a partial reflection mirror such as a dichroic mirror is preferred, since it introduces the fluorescence light to the detection elements with high efficiency. The transparent plate or the dichroic mirror is placed at an angle of 45° to the optical axis. The element plate is preferably thinner, since the thickness causes deviation of the optical axis, and has usually a thickness of about 1 mm. A combination prism constituted of two isosceles right triangle prisms glued together at the hypotenuse faces is suitable for achieving highly precise equivalence because the prism does not cause deviation of the optical axis of the transmitted light. Wavelength selectivity can be achieved by forming a multi-layered film at the glued interface.

Optionally, the first partial mirror is used as detection of a triggering event and to filter the exciting light. For example, where the light source emits at 488 nm and the fluorescent substance emits at 510 nm, then the first partial mirror may reflect at about 500 nm. The reflected light 63 is detected by any convenient light detecting element 72. The detection element may include photodiodes, phototransistors, and photomultipliers, but is not limited thereto.

A second light separation element 62 will usually be included. The second light separation element reflects the fluorescent light at a wavelength slightly higher than the peak emission wavelength of the fluorescent substrate. For example, where the fluorescent substrate is GFP, having a peak at 510 nm, then the light separation element may pass through light at greater than 520 nm, and reflect shorter wavelengths. Optionally the fluorescent light may be transmitted through an absorption filter 65 that transmits only light having a wavelength longer than a specified wavelength region. The fluorescence transmitted through the absorption filter is detected by the light detection element 73. The fluorescent light is detected, preferably by a photomultiplier, and the signal transmitted to a data processor 80.

There is generally an autofluorescent or background signal at a wavelength higher than that emitted from the fluorescent compound. For example, it has been found that Drosophila embryos have a high autofluorescent signal. This background light 34 is received by a light detection element 74, and the transduced signal transmitted to the data processor.

The light detection apparatus of this embodiment is characterized by the pair of detection elements 73 and 74, which are preferably arranged to be optically equivalent to each other relative to the light-separating element, meaning the arrangement of the two detection elements equalizes the changes of output signals from the two detection elements. The ratio of the changes in the detection elements, and thereby the intensity of the fluorescence is measured. The ratio determines whether a given particle is characterized as "positive" or "negative" for the fluorescent substance. Where there is an increase in the detection of fluorescence at the wavelength associated with the marker, relative to the autofluorescent light, then the particle is considered "positive". The level of signal required is pre-set, and determined by various factors, including levels of the substance present on the particle, number of cells or size of particle, autofluorescence, etc.

Figure 3A:
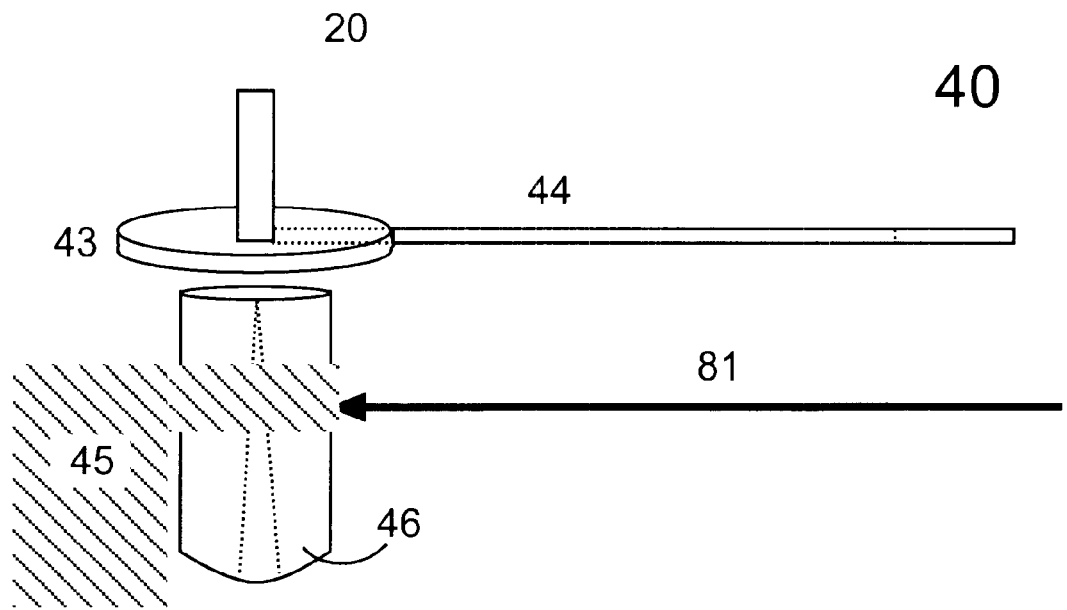
FIG. 3A is an expanded view of the switching apparatus.
Figure 3B:
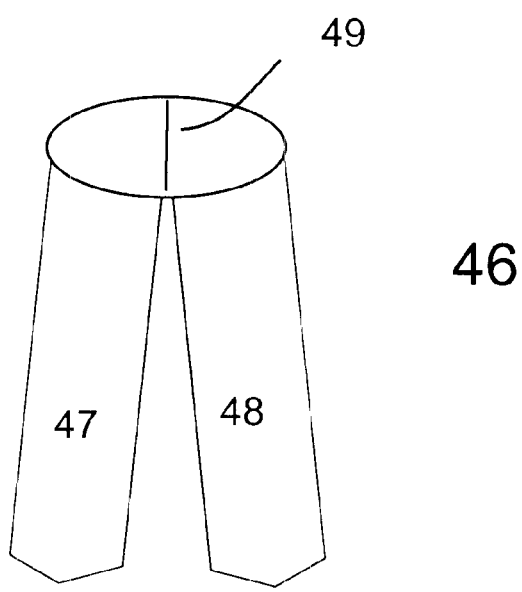
FIG. 3B illustrates the collection conduit.

FIGS. 3A and 3B illustrate features of the switching mechanism. The switching mechanism 40 controls the position of a collection conduit 46 between two set points: the first point being a collection set point for the collection of objects having a first phenotype and the second being a set point for the collection of objects having a second phenotype. The first and second phenotypes will usually correspond to high and low levels of fluorescence. In some embodiments of the invention, the first phenotype can correspond to a desired phenotype, and will be saved, while the second phenotype will be collected as waste. Alternatively, both phenotypes can be saved.

A variety of switches can be used in the sorter, including opposing solenoid valves that alternatively move the switching chamber, electromagnetic switches, and the like. For example, this assembly can be suspended between two electromagnets. Applying electric current to the electromagnets exerts force on the suspended magnet in one direction, moving the conduit. Reversing the current produces a force in the opposite direction.

The flow of particles 20 is merged with a high velocity fluid flow 44 which forces the particles to a switching chamber 40, which comprises a collection conduit 46 that is mechanically moved by a switch 45, which is controlled by a signal from the data processor 81. The conduit is composed of two tubes for collecting the two sorted phenotypes, 47 and 48, which separated by a very thin central wall 49, which may be a membrane or other very thin material. Sorting is achieved by moving the appropriate tube under the fluid stream.

Figure 4:
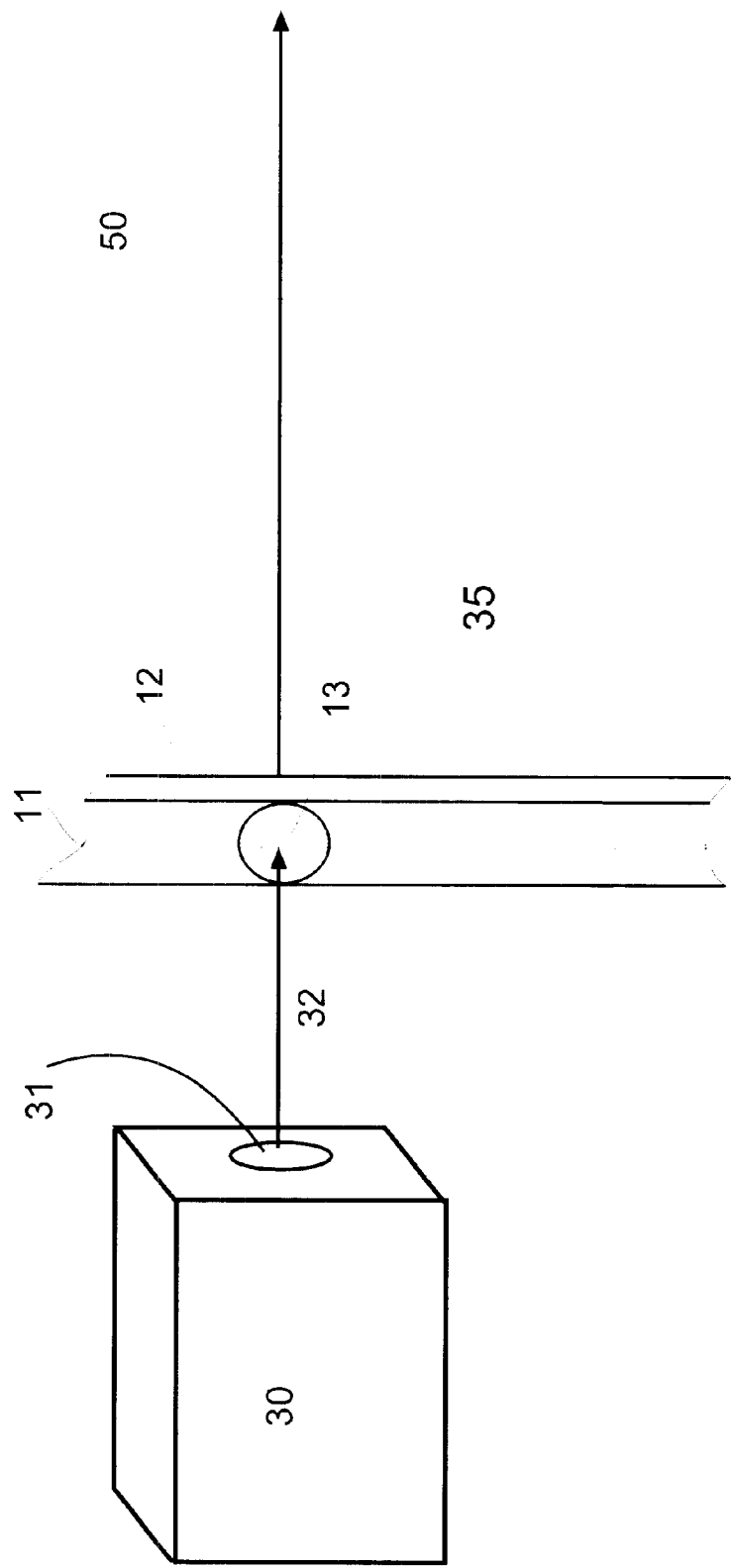
FIG. 4 is an expanded view of the optical chamber.

FIG. 4 is a detailed view of the optical cuvette 35. The exciting light source 30 is passed through a filter 31 to emit a beam of light 32 through a transparent window 13. An aperture is preferably provided near the light source to limit the optical path. The window provides a light path through the flow path 20, which is encase in a sheath 12. The light emitted from the particle is passed through focusing optics 50. Usually a lens is employed as the light focusing element. The curvature radius of the lens is selected suitably depending on the position of the beam. The lens system is generally constituted of two lens units, where each lens unit may be a single lens or a combination lens. The lens may be a double convex lens or a plano-convex lens.

Figure 5:
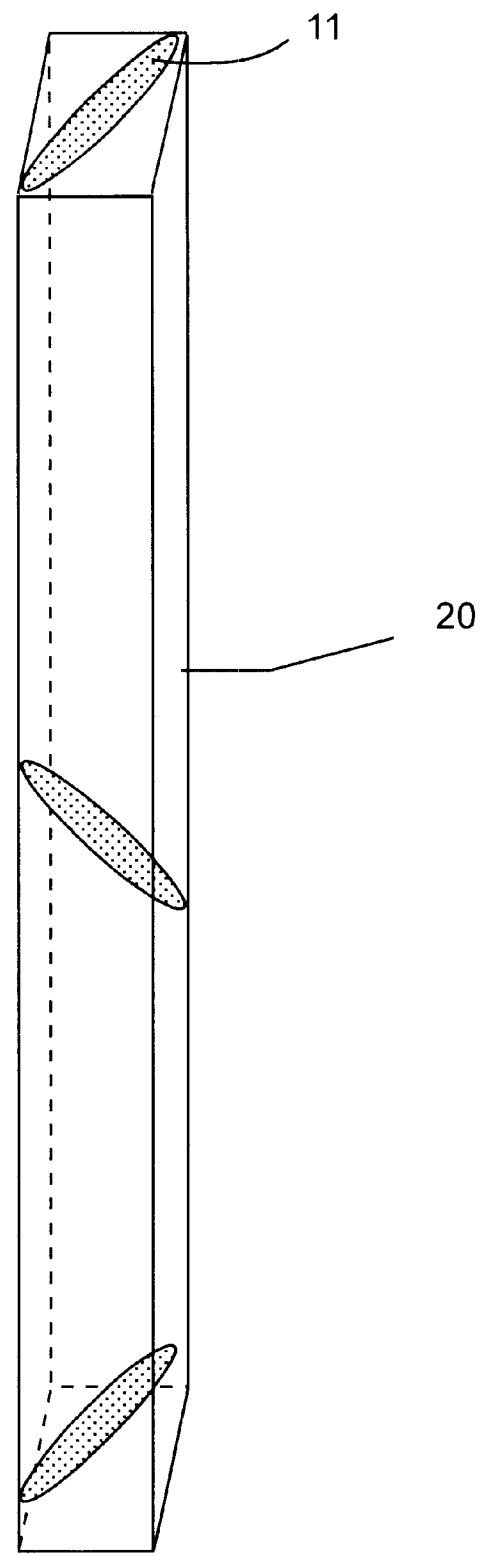
FIG. 5 is an expanded view of a liquid flow path.

In one embodiment of the invention, the flow path has the structure as shown in FIG. 5. In some instances there is found to be variable background light from the particles, which variability can be part be attributed to the movement of irregularly shaped particles in the flow. This is addressed by the use of a square or rectangular geometry for the flow path 20. The diagonal dimensions of the flow path orient the particles so that they must travel in a restricted configuration, thereby reducing the variability of signal.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the embryo" includes reference to one or more embryos and equivalents thereof known to those skilled in the art, and so forth. All technical and scientific terms used herein have the same meaning as commonly understood to one of ordinary skill in the art to which this invention belongs unless clearly indicated otherwise.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

EXAMPLE 1

Sorting of Drosophila Embryos

Drosophila embryos are placed in an embryo chamber and suspended in solution by gentle mixing using a magnetic stir plate. The embryo chamber is a sealed container with one opening at the top where solution is flowing in at a fixed rate and there is a second exit hole on the bottom. This creates a continuous flow of liquid through the chamber into which an embryo randomly enters. Once an embryo has exited the embryo chamber it enters a small diameter glass tube. The glass tube is embedded in a plastic sleeve that has a window for optical viewing.

Light from an argon laser is enters this window at one side of the tube, and on the other side of the tube is a series of lenses, diachronic mirrors and filters, and two photomultiplier tubes. Once an embryo has passed through this tune it is excited by the laser light and then any light emitted by the embryo is detected by the photomultipliers. While the machine is currently used for green fluorescent protein, it can be easily modified for use with other fluorochromes, such as luciferase, yellow fluorescent protein, blue fluorescent protein, cyan fluorescent protein, etc.

The S65T form of GFP is excited at 488 nm and emits light at 510 nm. Once the laser excites the GFP in the embryos, the emitted light is passed through a focusing mirror and then through a 500 nm long pass diachroic mirror. The light between 488–500 nm is detected by a diode, and a second diachroic mirror splits the light above 500 nm. Light between 500–520 nm is detected by a first photomultiplier, and the light between 520–600 nm is detected by a second photomultiplier as background fluorescence. A ratio is taken from the signal received by the two photomultipliers, i.e. the difference in fluorescence between GFP wavelengths and background intrinsic autofluorescence. If this ratio is above a defined threshold, indicating that the embryo contains GFP, a signal is sent to a mechanical switching device to direct the flow towards the waste. If the signal from the first photomultiplier is low, indicating that the embryo does not contain GFP, the switch directs the fluid flow to save that embryo in a collection container.

The amplitudes of light emitted from the embryos has been visualized by an oscilliscope, but in a preferred embodiment is connected to a computer. The computer allows for a highly sensitive system that can determine differences in fluorescence even when there is only a small percentage of GFP containing cells in each embryo. The computer program also allows the user to save the parameters between runs.

What is claimed is:

1. An automated particle sorter, comprising:
   a fluid flow path for passage of biological particles, which comprises an optical cuvette;
   a fluid ring over an end of said optical cuvette, wherein said fluid ring injects fluid into a particle stream as it exits said optical cuvette;
   a switch that alters the position of a collection conduit between two set points for sorting of particles according to their level of fluorescence;
   a light irradiation system comprising a light source that emits light through said cuvette at a wavelength that causes fluorescence excitement;
   a light detection apparatus comprising at least two detection elements for measuring emitted fluorescence; and
   a data processor that receives signals from said light detection elements and according to pre-set parameters, controls said switch to physically sort said particles.

2. The particle sorter of claim 1, wherein said light irradiation system comprises a laser, a filter and focusing optics.

3. The particle sorter of claim 1, wherein said light detection apparatus comprises one or more light separation elements.

4. The particle sorter of claim 3, wherein said light separation elements are diachroic mirrors that reflect fluorescent light at a wavelength below said wavelength that causes fluorescence excitement.

5. The particle sorter of claim 4, wherein said light detection elements comprise two or more photomultiplier tubes.

6. The particle sorter of claim 5, wherein said switch is a switch that moves a collection conduit.

7. The particle sorter of claim 1, wherein said collection conduit comprises two tubes separated by a thin membrane.

8. The particle sorter of claim 1, wherein said fluid flow path is an elongated member of square or rectangular cross-sectional geometry, wherein the positions of said particles in the particles are constrained.

9. An automated particle sorter, comprising:

a fluid flow path for passage of biological particles, which comprises an optical cuvette and a high density particle chamber and a low density particle chamber, wherein the high density particle chamber and low density particle chambers are connected by a fluid valve controlled by a data processor, and particle density in said fluid flow path is maintained at a predetermined level by opening and closing of said fluid valve;

a switch that alters the position of a collection conduit between two set points for sorting of particles according to their level of fluorescence;

a light irradiation system comprising a light source that emits light through said cuvette at a wavelength that causes fluorescence excitement;

a light detection apparatus comprising at least two detection elements for measuring emitted fluorescence; and a data processor that receives signals from said light detection elements and according to pre-set parameters, controls said switch to physically sort said particles.

10. The particle sorter of claim 9, wherein said low density particle chamber comprises a magnetic stir bar set on a pin.

11. A method of sorting biological particles according to their level of fluorescence, the method comprising:

suspending said particles in solution;

moving said suspension through a liquid flow path comprising an optical cuvette through which a light is emitted at a wavelength that excites a fluorescent compound on the particles;

detecting the level of fluorescence on said particles by at least two light detection elements, wherein a signal from said light detection elements is received by a data processor that controls a switch that alters the position of a collection conduit between two set points;

merging said suspension with a high velocity fluid flow as said suspension exits said optical cuvette that forces the particles into said collection conduit; and moving said collection conduit between said two set points in accordance with the level of fluorescence associated with said particles.

12. The method of claim 11, wherein said particles are whole animals of from 10 to 105 cells in size.

13. The method of claim 12, wherein said whole animals are viable embryos.

14. The method of claim 12, wherein said fluorescent compound is a protein expressed by and associated with said animal.

15. The method of claim 12, wherein said animals are Drosophila embryos expressing green fluorescent protein.

* * * * *